(12) United States Patent
Schindler et al.

(10) Patent No.: US 7,034,195 B2
(45) Date of Patent: Apr. 25, 2006

(54) METHOD FOR THE PRODUCTION OF BUTADIENE FROM N-BUTANE

(75) Inventors: Götz-Peter Schindler, Mannheim (DE); Christian Walsdorff, Ludwigshafen (DE); Klaus Harth, Altleiningen (DE); Hartmut Hibst, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/516,920

(22) PCT Filed: Jul. 10, 2003

(86) PCT No.: PCT/EP03/07523

§ 371 (c)(1),
(2), (4) Date: Dec. 7, 2004

(87) PCT Pub. No.: WO2004/007408

PCT Pub. Date: Jan. 22, 2004

(65) Prior Publication Data

US 2005/0171311 A1     Aug. 4, 2005

(30) Foreign Application Priority Data

Jul. 12, 2002 (DE) .............................. 102 31 632

(51) Int. Cl.
*C07C 5/333* (2006.01)
(52) U.S. Cl. .................. 585/633; 585/616; 585/627
(58) Field of Classification Search ................ 585/633, 585/627, 616
See application file for complete search history.

(56) References Cited

U.S. PATENT DOCUMENTS

| 2,376,323 | A | * | 5/1945 | Boatright, Jr. et al. ....... 585/602 |
| 3,161,670 | A | * | 12/1964 | Adams et al. .............. 558/320 |
| 3,907,919 | A | * | 9/1975 | Lo et al. ..................... 585/617 |
| 4,504,692 | A | * | 3/1985 | Arakawa et al. ............ 585/633 |

FOREIGN PATENT DOCUMENTS

| GB | 508764 | 7/1939 |
| GB | 628686 | 4/1947 |
| GB | 1107432 | 3/1968 |
| GB | 1391649 | 4/1975 |

* cited by examiner

*Primary Examiner*—Fred Teskin
(74) *Attorney, Agent, or Firm*—Novak Druce DeLuca & Quigg, LLP

(57) ABSTRACT

The invention relates to a process for preparing butadiene from n-butane comprising the steps
(A) providing an n-butane-containing feed gas stream,
(B) feeding the n-butane-containing feed gas stream into a first dehydrogenation zone and nonoxidatively catalytically dehydrogenating n-butane to 1-butene, 2-butene and optionally butadiene to obtain a first product gas stream comprising n-butane, 1-butene and 2-butene, with or without butadiene and secondary components,
(C) feeding the first product gas stream comprising n-butane, 1-butene and 2-butene, with or without butadiene and secondary components, into a second dehydrogenation zone and oxidatively dehydrogenating 1-butene and 2-butene to butadiene to give a second product gas stream comprising butadiene, n-butane and steam, with or without secondary components,
(D) recovering butadiene from the second product gas stream.

4 Claims, 1 Drawing Sheet

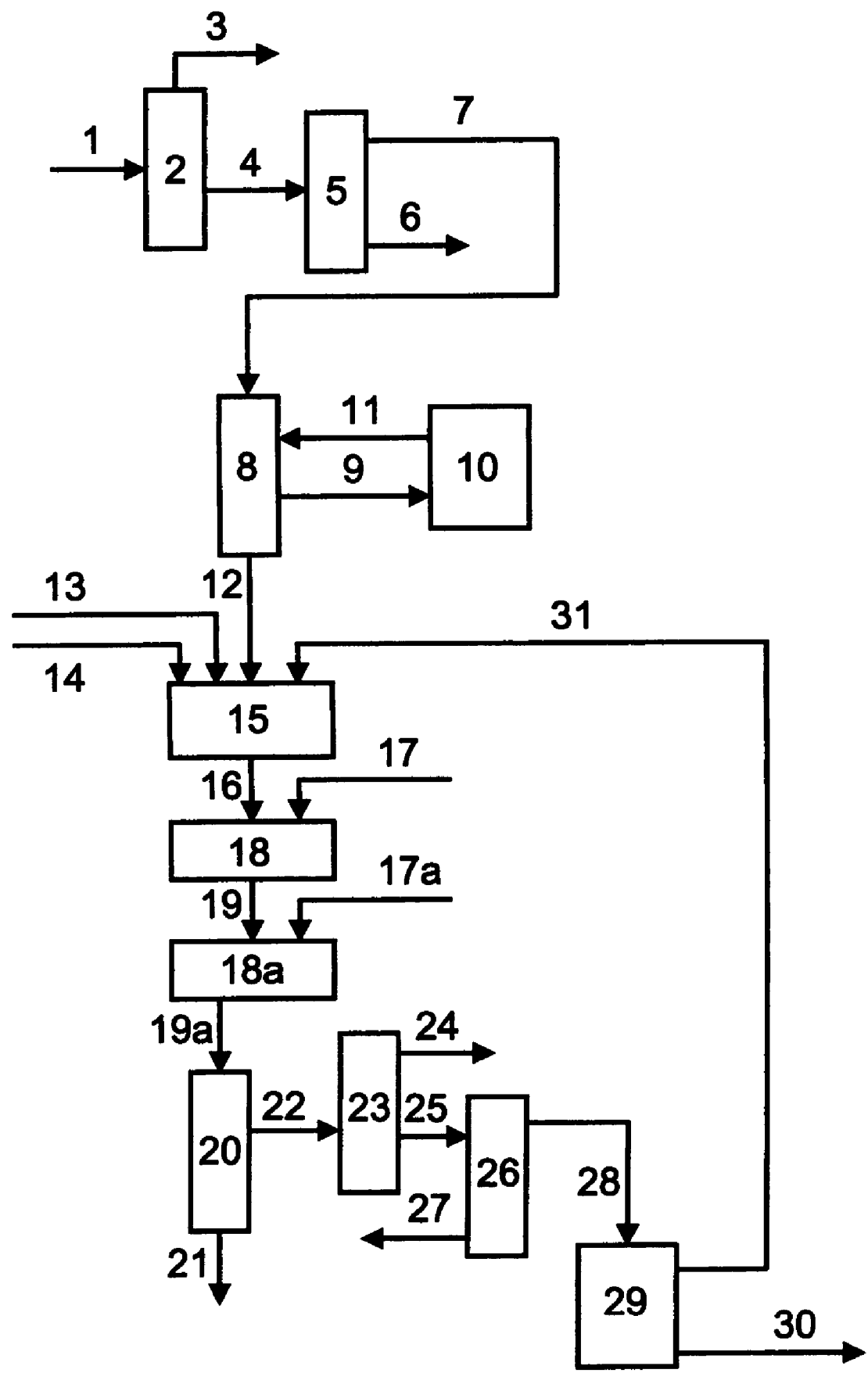

METHOD FOR THE PRODUCTION OF BUTADIENE FROM N-BUTANE

Butadiene is prepared predominantly by thermal cleavage (cracking) of saturated hydrocarbons, customarily starting from naphtha as the raw material. Cracking of naphtha results in a hydrocarbon mixture of methane, ethane, ethene, acetylene, propane, propene, propyne, allene, butenes, butadiene, butynes, methylallene, $C_5$ and higher hydrocarbons. Acetylenically unsaturated hydrocarbons in the cracking gas such as acetylene, propyne, 1-butyne, 2-butyne, butenyne and diacetylene may interfere, for example, in a subsequent dimerization of butadiene in a Diels-Alder reaction to vinylcyclohexane, since even traces of these compounds can poison the copper dimerization catalyst. Butynes and allenes likewise react with butadiene in a Diels-Alder reaction and lead to by-product formation. Triply unsaturated $C_4$ hydrocarbons are generally also troublesome in other uses of butadiene.

The butynes in particular, which can only be removed distillatively or extractively from butadiene with great difficulty, present problems. It is therefore necessary when using butadiene from crackers to precede the butadiene dimerization with a hydrogenation stage in which the butynes are selectively partially hydrogenated to the corresponding butenes.

A further disadvantage is that when cracking naphtha or other hydrocarbon mixtures, a complex hydrocarbon mixture is obtained. For instance, when butadiene is obtained in the cracking process, relatively large amounts of ethene or propene are inevitably obtained as coproducts.

Alternatively, butadiene can be prepared starting from n-butane by catalytic dehydrogenation. However, a disadvantage of this process is the low butadiene yield, since the catalytic dehydrogenation of n-butane results predominantly in 1-butene and 2-butene.

It is an object of the present invention to provide a process for preparing butadiene from n-butane which does not have the disadvantages of the prior art and allows high butadiene yields to be obtained.

We have found that this object is achieved by a process for preparing butadiene from n-butane comprising the steps of
(A) providing an n-butane-containing feed gas stream,
(B) feeding the n-butane-containing feed gas stream into a first dehydrogenation zone and nonoxidatively catalytically dehydrogenating n-butane to 1-butene, 2-butene and optionally butadiene to obtain a first product gas stream comprising n-butane, 1-butene and 2-butene, with or without butadiene and secondary components,
(C) feeding the first product gas stream comprising n-butane, 1-butene and 2-butene, with or without butadiene and secondary components, into a second dehydrogenation zone and oxidatively dehydrogenating 1-butene and 2-butene to butadiene to give a second product gas stream comprising butadiene, n-butane and steam, with or without secondary components,
(D) recovering butadiene from the second product gas stream.

In a first process part A, an n-butane-containing feed gas stream is provided. Customarily, the raw material is an n-butane-rich gas mixture such as liquefied petroleum gas (LPG).

LPG substantially comprises $C_2$–$C_5$-hydrocarbons. The composition of LPG may vary widely. Advantageously, the LPG used comprises at least 10% by weight of butanes.

In one variant of the process according to the invention, the provision of the n-butane-containing dehydrogenation feed gas stream comprises the steps of
(A1) providing a liquefied petroleum gas (LPG) stream,
(A2) removing propane and optionally methane, ethane and pentanes from the LPG stream to obtain a butane- (n-butane- and isobutane-) containing stream,
(A3) removing isobutane from the butane-containing stream to obtain the n-butane-containing feed gas stream and optionally isomerizing the removed isobutane to an n-butane/isobutane mixture and recycling the n-butane/isobutane mixture into the isobutane removal.

Propane and any methane, ethane and pentanes are removed in one or more customary rectification columns. For example, low boilers (methane, ethane, propane) can be removed overhead in a first column and high boilers (pentanes) removed at the column bottom in a second column. A stream comprising butanes (n-butane and isobutane) is obtained from which isobutane is removed, for example in a customary rectification column. The remaining n-butane-containing stream is used as the feed gas stream for the subsequent butane dehydrogenation.

Preference is given to subjecting the removed isobutane stream to isomerization. To this end, the isobutane-containing stream is fed into an isomerization reactor. The isomerization of isobutane to n-butane can be carried out as described in GB-A 2 018 815.

An n-butane/isobutane mixture is obtained which is fed into the n-butane/isobutane separating column.

In a process part (B), the n-butane-containing feed gas stream is fed into a first dehydrogenation zone and subjected to a nonoxidative catalytic dehydrogenation. n-Butane is partially dehydrogenated in a dehydrogenation reactor over a dehydrogenating catalyst to 1-butene and 2-butene, and small amounts of butadiene may also be formed. In addition, hydrogen and small amounts of methane, ethane, ethene, propane and propene are formed. Depending on the dehydrogenation method, carbon oxides (CO, $CO_2$), water and nitrogen may also be present in the product gas mixture of the nonoxidative catalytic n-butane dehydrogenation. In addition, unconverted n-butane is present in the product gas mixture.

The nonoxidative catalytic n-butane dehydrogenation may be carried out with or without oxygen-containing gas as a cofeed.

A feature of the nonoxidative method compared to an oxidative method is the presence of hydrogen in the effluent gas. In the oxidative dehydrogenation, no substantial amounts of free hydrogen are formed.

In principle, the nonoxidative catalytic n-butane dehydrogenation may be carried out in all reactor types and methods known from the prior art. A comparatively comprehensive description of dehydrogenation processes suitable according to the invention may also be found in "Catalytica® Studies Division, Oxidative Dehydrogenation and Alternative Dehydrogenation Processes" (Study Number 4192 OD, 1993, 430 Ferguson Drive, Mountain View, Calif. 94043-5272, USA).

A suitable reactor form is a fixed bed tubular or tube bundle reactor. In these reactors, the catalyst (dehydrogenation catalyst and, when working with oxygen as the cofeed, optionally a special oxidation catalyst) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1 000 reaction tubes. The internal temperature in the reaction tubes is customarily in the range from 300 to 1 200° C., preferably in the range from 500 to 1 000° C. The working pressure is customarily from 0.5 to 8 bar, frequently from 1 to 2 bar, when a small steam dilution is used (similar to the Linde process for propane dehydrogenation), or else from 3 to 8 bar when using a high steam dilution (similar to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical gas hourly space velocities (GSHV) are from 500 to 2 000 $^{-1}$, based on the hydrocarbon used. The catalyst geometry may, for example, be spherical or cylindrical (hollow or solid).

The nonoxidative catalytic n-butane dehydrogenation may also be carried out under heterogeneous catalysis in a fluidized bed, as described in Chem. Eng. Sci. 1992 b, 47 (9–11) 2313. Advantageously, two fluidized beds are operated in parallel, of which one is generally in the process of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature. The admixing of an oxygen-containing cofeed allows the preheater to be dispensed with and the required heat can be generated directly in the reactor system by combustion of hydrogen in the presence of oxygen. Optionally, a hydrogen-containing cofeed may additionally be admixed.

The nonoxidative catalytic n-butane dehydrogenation may be carried out in a tray reactor with or without oxygen-containing gas as cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. Carrying out the dehydrogenation in a single shaft furnace reactor corresponds to a preferred embodiment, where the oxygen-containing cofeed may be used. In a further preferred embodiment, the dehydrogenation is carried out in a tray reactor having three catalyst beds. In a method without oxygen-containing gas as cofeed, the reaction gas mixture is subjected to a degree of heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partially combusted which directly generates in the reaction gas mixture at least a portion of the heat required for dehydrogenation in the at least one reaction zone.

In general, the amount of oxygen-containing gas added to the reaction gas mixture is chosen in such a manner that the amount of heat required for the dehydrogenation of n-butane is generated by the combustion of the hydrogen present in the reaction gas mixture and any hydrocarbons present in the reaction gas mixture and/or carbon present in the form of coke. In general, the total amount of oxygen fed in, based on the total amount of butane, is from 0.001 to 0.5 mol/mol, preferably from 0.005 to 0.2 mol/mol, more preferably from 0.05 to 0.2 mol/mol. Oxygen may be used either as pure oxygen or as an oxygen-containing gas in the mixture with inert gases, for example in the form of air. The inert gases and the gases resulting from the combustion generally provide additional dilution and therefore support the heterogeneously catalyzed dehydrogenation.

The hydrogen combusted to generate heat is the hydrogen formed in the catalytic n-butane dehydrogenation and also any hydrogen additionally added to the reaction gas mixture as hydrogen-containing gas. The quantity of hydrogen present should preferably be such that the $H_2/O_2$ molar ratio in the reaction gas mixture immediately after the oxygen is fed in is from 1 to 10 mol/mol, preferably from 2 to 5 mol/mol. In multistage reactors, this applies to every intermediate feed of oxygen-containing and any hydrogen-containing gas.

The hydrogen is combusted catalytically. The dehydrogenation catalyst used generally also catalyzes the combustion of the hydrocarbons and of hydrogen with oxygen, so that in principle no additional specialized oxygenation catalyst is required. In one embodiment, operation is effected in the presence of one or more oxidation catalysts which selectively catalyze the combustion of hydrogen to oxygen in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one, in more than one or in all reaction zones.

Preference is given to disposing the catalyst which selectively catalyzes the oxidation of hydrogen at the points where there are higher oxygen partial pressures than at other points in the reactor, in particular near the feed point for the oxygen-containing gas. The oxygen-containing gas and/or hydrogen-containing gas may be fed in at one or more points in the reactor.

In one embodiment of the process according to the invention, there is intermediate feeding of oxygen-containing gas and of hydrogen-containing gas upstream of each tray of a tray reactor. In a further embodiment of the process according to the invention, oxygen-containing gas and hydrogen-containing gas are fed in upstream of each tray except the first tray. In one embodiment, a layer of a specialized oxygenation catalyst is present downstream of every feed point, followed by a layer of the dehydrogenation catalyst. In a further embodiment, no specialized oxidation catalyst is present. The dehydrogenation temperature is generally from 400 to 1 100° C., the pressure in the last catalyst bed of the tray reactor is generally from 0.2 to 5 bar, preferably from 1 to 3 bar. The GSHV is generally from 500 to 2 000 $h^{-1}$, and in a high-load operation, even up to 100 000 $h^{-1}$, preferably from 4 000 to 16 000 $h^{-1}$.

A preferred catalyst which selectively catalyzes the combustion of hydrogen comprises oxides and/or phosphates selected from the group consisting of oxides and/or phosphates or germanium, tin, lead, arsenic, antimony and bismuth. A further preferred catalyst which catalyzes the combustion of hydrogen comprises a noble metal of transition group VIII and/or I of the periodic table.

The dehydrogenation catalysts used generally comprise a support and an active composition. The support generally consists of a heat-resistant oxide or mixed oxide. The dehydrogenation catalysts preferably comprise a metal oxide selected from the group consisting of zirconium oxide, zinc oxide, aluminum oxide, silicon dioxide, titanium dioxide, magnesium oxide, lanthanum oxide, cerium oxide and mixtures thereof, as support. The mixtures may be physical mixtures or else chemical mixed phases of magnesium aluminum oxide or zinc aluminum oxide mixed oxides. Preferred supports are zirconium dioxide and/or silicon dioxide, and particular preference is given to mixtures of zirconium dioxide and silicon dioxide.

The active composition of the dehydrogenation catalysts generally comprises one or more metals of transition group VIII of the periodic table, preferably platinum and/or palladium, more preferably platinum. Furthermore, the dehydrogenation catalysts may comprise one or more elements of main group I and/or II of the period table, preferably potassium and/or cesium. The dehydrogenation catalysts may further comprise one or more elements of transition group III of the period table including the lanthanides and actinides, preferably lanthanum and/or cerium. Finally, the dehydrogenation catalysts may comprise one or more elements of main group III and/or IV of the periodic table, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides, of the periodic table.

For example, all dehydrogenation catalysts which are disclosed by WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used according to the invention. Particularly preferred catalysts for the above-described variants of autothermal n-butane dehydrogenation are the catalysts according to examples 1, 2, 3 and 4 of DE-A 199 37 107.

Preference is given to carrying out the n-butane dehydrogenation in the presence of steam. The added steam serves as a heat carrier and supports the gasification of organic deposits on the catalysts, which counteracts carbonization of the catalysts and increases the on stream time of the catalysts. The organic deposits are converted to carbon monoxide, carbon dioxide and possibly water.

The dehydrogenation catalysts may be regenerated in a manner known per se. For instance, steam may be added to the reaction mixture or an oxygen-containing gas may be passed from time to time over the catalyst bed at elevated temperature and the deposited carbon burnt off. Dilution with steam shifts the equilibrium toward the products of dehydrogenation. After the regeneration with steam, the catalyst is optionally reduced with a hydrogen-containing gas.

The n-butane dehydrogenation provides a gas mixture which, in addition to butadiene, 1-butene, 2-butene and unconverted n-butane, comprises secondary components. Customary secondary components include hydrogen, steam, nitrogen, CO and $CO_2$, methane, ethane, ethene, propane and propene. The composition of the gas mixture leaving the first dehydrogenation zone may be highly variable depending on the dehydrogenation method. For instance, in the preferred autothermal dehydrogenation with feeding in of oxygen and in addition of hydrogen, the product gas mixture comprises a comparatively high content of steam and carbon oxides. In methods without feeding in of oxygen, the product gas mixture of the nonoxidative dehydrogenation has a comparatively high hydrogen content.

The product gas stream of the nonoxidative autothermal n-butane dehydrogenation typically comprises from 0.1 to 15% by volume of butadiene, from 1 to 15% by volume of 1-butene, from 1 to 20% by volume of 2-butene, from 20 to 70% by volume of n-butane, from 5 to 70% by volume of steam, from 0 to 5% by volume of low-boiling hydrocarbons (methane, ethane, ethene, propane and propene), from 0 to 30% by volume of hydrogen, from 0 to 30% by volume of nitrogen and from 0 to 5% by volume of carbon oxides.

According to the invention, the nonoxidative catalytic dehydrogenation is followed by an oxidative dehydrogenation (oxydehydrogenation) as process part C.

In principle, this may be carried out in all reactor types and methods known from the prior art, for example in a fluidized bed, in a tray furnace or a fixed bed tubular or tube bundle reactor. Preference is given to using the latter in the process according to the invention. To carry out the oxydehydrogenation, a gas mixture is required which has a molar oxygen: n-butene ratio of at least 0.5. Preference is given to an oxygen: n-butene ratio of from 0.55 to 50. To adjust this ratio, the product gas mixture which generally results from the catalytic dehydrogenation is mixed with oxygen or an oxygen-containing gas, for example air. The oxygen-containing gas mixture obtained is then fed to the oxydehydrogenation.

The catalysts which are particularly suitable for the oxydehydrogenation of the n-butenes to 1,3-butadiene are generally based on an Mo—Bi—O multimetal oxide system which generally additionally comprises iron. In general, the catalyst system also comprises additional components from groups 1 to 15 of the periodic table, for example potassium, magnesium, zirconium, chromium, nickel, cobalt, cadmium, tin, lead, germanium, lanthanum, manganese, tungsten, phosphorus, cerium, aluminum or silicon.

Useful catalysts and their preparation are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$+$SiO_2$) and DE-A 24 40 329 ($Mo_{12}BiCo_{4.5}Ni_{2.5}Cr_3P_{0.5}K_{0.1}O_x$), which are explicitly incorporated herein by way of reference.

The stoichiometry of the active composition of a variety of multimetal oxide catalysts suitable for the oxydehydrogenation of the n-butenes to 1,3-butadiene can be subsumed under the general formula (I)

$$Mo_{12}Bi_aFe_bCo_cNi_dCr_eX^1_fK_gO_x \tag{I}$$

where the variables are defined as follows:
$X^1$=W, Sn, Mn, La, Ce, Ge, Ti, Zr, Hf, Nb, P, Si, Sb, Al, Cd and/or Mg;
a=from 0.5 to 5, preferably from 0.5 to 2;
b=from 0 to 5, preferably from 2 to 4;
c=from 0 to 10, preferably from 3 to 10;
d=from 0 to 10;
e=from 0 to 10, preferably from 0.1 to 4;
f=from 0 to 5, preferably from 0.1 to 2;

g=from 0 to 2, preferably from 0.01 to 1; and
x=a number which is determined by the valency and frequency of the elements in (I) other than oxygen.

In the process according to the invention, preference is given to using an Mo—Bi—Fe—O multimetal oxide system for the oxydehydrogenation, and particular preference is given to a Mo—Bi—Fe—Cr—O or Mo—Bi—Fe—Zr—O metal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($MO_{12}BiFe_3CO_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}Ox$ and $Mo_{12}BiFe_3Co_{4.5}Ni_{2.5}La_{0.5}K_{0.1}O_x$), U.S. Pat. No. 3,911,039 ($MO_{12}BiFe_3CO_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$). The preparation and characterization of the catalysts mentioned are described comprehensively in the documents cited to which reference is hereby explicitly made.

The oxydehydrogenation catalyst is generally used as shaped bodies having an average size of over 2 mm. Owing to the pressure drop to be observed when performing the process, smaller shaped bodies are generally unsuitable. Examples of useful shaped bodies include tablets, cylinders, hollow cylinders, rings, spheres, strands, wagon wheels or extrudates. Special shapes, for example "trilobes" and "tristars" (see EP-A-0 593 646) or shaped bodies having at least one notch on the exterior (see U.S. Pat. No. 5,168,090) are likewise possible.

In general, the catalysts used may be used as an unsupported catalyst. In this case, the entire shaped catalyst body consists of the active composition, including any auxiliary, such as graphite or pore former and also further components. In particular, it has proven advantageous to use the Mo—Bi—Fe—O catalyst preferably used for the oxydehydrogenation of n-butenes to butadiene as an unsupported catalyst. Furthermore, it is possible to apply the active compositions of the catalysts to a support, for example an inorganic, oxidic shaped body. Such catalysts are generally referred to as coated catalysts.

The oxydehydrogenation of the n-butenes to butadiene is generally carried out at a temperature of from 220 to 490° C. and preferably from 250 to 450° C. For practical reasons, a reactor entrance pressure is generally chosen which is sufficient to overcome the flow resistances in the plant and the subsequent workup. This reactor entrance pressure is generally from 0.005 to 1 MPa above atmospheric pressure, preferably from 0.01 to 0.5 MPa above atmospheric pressure. By its nature, the gas pressure applied in the entrance region of the reactor substantially falls over the entire catalyst bed and inert fractions.

The coupling of the nonoxidative catalytic, preferably autothermal dehydrogenation with the oxidative dehydrogenation of the n-butenes formed provides a very much higher yield of butadiene based on n-butane used. The nonoxidative dehydrogenation can also be operated in a gentler manner. Comparable yields would only be achievable with an exclusively nonoxidative dehydrogenation at the cost of distinctly reduced selectivities.

In addition to butadiene and unconverted n-butane, the second product gas stream leaving the oxydehydrogenation comprises steam. As secondary components it generally comprises carbon monoxide, carbon dioxide, oxygen, nitrogen, methane, ethane, ethene, propane and propene, with or without hydrogen and also oxygen-containing hydrocarbons, known as oxygenates. In general, it only comprises very small proportions of 1-butene and 2-butene.

For example, the product gas stream leaving the oxydehydrogenation may comprise from 1 to 20% by volume of butadiene, from 0 to 1% by volume of 1-butene, from 0 to 1% by volume of 2-butene, from 0 to 50% by volume of butane, from 2 to 50% by volume of steam, from 0 to 5% by volume of low-boiling hydrocarbons (methane, ethane, ethene, propane and propene), from 0 to 20% by volume of hydrogen, from 0 to 90% by volume of nitrogen, from 0 to 5% by volume of carbon oxides and from 0 to 3% by volume of oxygenates.

Butadiene is recovered in a process part D from the second product gas stream obtained in the oxydehydrogenation.

The recovery of butadiene from the second product gas stream may comprise the following steps:

(D1) cooling the product gas stream with water to condense out steam and any high-boiling organic secondary components;

(D2) removing the low-boiling secondary components contained in the second product gas stream which are selected from the group consisting of hydrogen, carbon monoxide, carbon dioxide, nitrogen, methane, ethane, ethene, propane and propene, to obtain a stream comprising butadiene and n-butane, with or without 1-butene and 2-butene, and with or without oxygenates as further secondary components;

(D3) optionally removing the oxygenates to obtain a stream comprising butadiene and n-butane, with or without 1-butene and 2-butene;

(D4) separating the stream comprising butadiene and n-butane, with or without 1-butene and 2-butene, into a stream comprising n-butane, with or without 1-butene and 2-butene, and a stream comprising butadiene;

(D5) optionally recycling the stream comprising n-butane, with or without 1-butene and 2-butene, into the nonoxidative catalytic dehydrogenation (B).

After leaving the dehydrogenation stages, the hot gas mixture whose temperature is generally from 220 to 490° C. is customarily cooled with water. This condenses out steam and any high-boiling organic secondary components.

The low-boiling secondary components such as hydrogen, carbon monoxide, carbon dioxide, nitrogen, methane, ethane, ethene, propane and propene present in the dehyrogenation gas mixture in addition to butadiene, n-butane and any 1-butene and 2-butene are subsequently removed from the $C_4$ hydrocarbons.

The low-boiling secondary components may be removed by customary rectification.

The low-boiling secondary components may also be removed in an absorption/desorption cycle using a high-boiling absorbent. In this way, substantially all low-boiling secondary components (nitrogen, hydrogen, methane, ethane, ethene, propane, propene, carbon oxides, oxygen) are removed from the n-butane dehydrogenation product gas stream.

To this end, the $C_4$-hydrocarbons are absorbed in an inert absorbent in an absorption stage to obtain a $C_4$-hydrocarbon-laden absorbent and an offgas comprising the remaining secondary components. In a desorption stage, the $C_4$-hydrocarbon and traces of secondary components are released again from the absorbent.

Inert absorbents used in the absorption stage are generally high-boiling nonpolar solvents in which the hydrocarbon which is to be removed has a distinctly higher solubility than the remaining components of the product gas mixture. The absorption may be effected by simply passing the product gas mixture through the absorbent. However, it may also be effected in columns or in rotary absorbers. Operation may be effected in cocurrent, countercurrent or crosscurrent. Examples of useful absorption columns include tray columns having bubble, centrifugal and/or sieve trays, columns having structured packings, for example sheet metal packings having a specific surface area of from 100 to 1 000 $m^2/m^3$ such as Mellapak® 250 Y, and randomly packed columns. However, useful absorption columns also include trickle and spray towers, graphite block absorbers, surface absorbers such as thick-film and thin-film absorbers and also rotary columns, plate scrubbers, cross-space scrubbers and rotary scrubbers.

Useful absorbents are comparatively nonpolar organic solvents, for example aliphatic $C_8$-to $C_{18}$-alkenes, or aromatic hydrocarbons such as the middle oil fractions from paraffin distillation, or ethers having bulky groups, or mixtures of these solvents, to each of which a polar solvent such as 1,2-dimethyl phthalate may be added. Further useful absorbents include esters of benzoic acid and phthalic acid with straight-chain $C_1$–$C_8$-alkanols, such as n-butyl benzoate, methyl benzoate, ether benzoate, dimethyl phthalate, diethyl phthalate, and also heat carrier oils, such as biphenyl and diphenyl ether, their chlorine derivatives and also triarylalkenes. A useful absorbent is a mixture of biphenyl and diphenyl ether, preferably in the azeotropic composition, for example the commercially available Diphyl®. Frequently, this solvent mixture comprises dimethyl phthalate in an amount of 0.1 to 25% by weight. Further useful absorbents are octanes, nonanes, decanes, undecanes, dodecanes, tridecanes, tetradecanes, pentadecanes, hexadecanes, heptadecanes and octadecanes, or fractions obtained from refinery streams which have linear alkanes mentioned as main components.

For desorption, the laden absorbent is heated and/or decompressed to a lower pressure. Alternatively, desorption may also be effected by stripping or in a combination of decompression, heating and stripping in one or more process steps. The absorbent regenerated in the desorption stage is recycled into the absorption stage.

A stream consisting substantially of butadiene and n-butane remains which may also comprise 1-butene and 2-butene and also oxygenates as further secondary components. Such oxygenates include, for example, furan and maleic anhydride. The oxygenates may be removed from the $C_4$ hydrocarbons in a further separating stage which may likewise be configured as an absorption/desorption stage or as a rectification.

The remaining stream which customarily consists predominantly of butadiene and n-butane and, in addition, may also comprise small amounts of 1-butene and 2-butene may be separated in a further separating stage in a stream comprising n-butane and any 1-butene and 2-butene, and a stream comprising butadiene. The separation may be effected, for example, by butadiene scrubbing. Butadiene scrubbing may be effected as described in Weissermehl/Arpe, Industrielle Organische Chemie, $5^{th}$ Edition 1998, p. 120/121, or Hydrocarbon Processing, Mar. 2002, p. 50B.

The stream comprising n-butane and any 1-butene and 2-butene may at least partially be recycled into the nonoxidative catalytic dehydrogenation (B).

Process part (D) preferably comprises at least the steps (D1), (D2) and (D4). More preferably, it comprises the steps (D1) to (D5).

The invention is illustrated hereinbelow with reference to the drawing.

BRIEF DESCRIPTION OF THE DRAWING

The FIGURE shows the process flow diagram of a preferred embodiment of the process according to the invention.

A feed stream 1 of liquefied petroleum gas (LPG) which consists substantially of propane, n-butane and isobutane and, in addition, may also comprise methane, ethane or pentanes, is fed to a rectification column 2 and separated into a stream 3 composed substantially of propane and any methane and ethane, and a stream 4 composed substantially of n-butane and isobutane and any pentanes. In the rectification column 5, any pentanes 6 are removed. The butane mixture 7 is separated in the rectification column 8 into isobutane 9 and n-butane 12, and isobutane is isomerized in the isomerization reactor 10 to an n-butane/isobutane mixture 11 which is fed back into the rectification column 8. n-Butane is fed as the feed gas stream 12 into the first dehydrogenation stage 15 in which a nonoxidative catalytic dehydrogenation of butane to 1-butene, 2-butene and butadiene takes place. This is preferably carried out under autothermal conditions while feeding in oxygen or air as cofeed 13 and optionally hydrogen as cofeed 14. Preference is given to carrying out the first dehydrogenation stage with backmixing in a fluidized bed or with partial gas recycling, for example as described in German patent application P 102 11 275.4, unpublished at the Priority date of the present invention. The product gas stream 16 leaving the first dehydrogenation stage which, in addition to butadiene, 1-butene, 2-butene and unconverted n-butane, comprises steam and customary secondary components such as hydrogen, carbon oxides, nitrogen, hydrogen, methane, ethane, ethene, propane and propene is fed to a second dehydrogenation stage 18, in which while feeding in oxygen or air as cofeed 17, an oxydehydrogenation of 1-butene and 2-butene to butadiene takes place. The second dehydrogenation stage is preferably carried out in a tube bundle reactor. The second dehydrogenation stage may itself be carried out in more than one stage, for example in two stages. In the two-stage configuration of the oxydehydrogenation, the second dehydrogenation stage consists of a first oxydehydrogenation stage 18 and a second oxydehydrogenation stage 18a, into each of which air or oxygen is fed as cofeed 17 or 17a. The product gas stream 19a leaving the second dehydrogenation stage (in the one-stage configuration of the oxydehydrogenation, this is the product gas stream 19) comprises, in addition to butadiene and unconverted n-butane, steam and secondary components such as hydrogen, carbon oxides, nitrogen, methane, ethane, ethene, propane and/or propene, with or without small residues of 1-butene and 2-butene and with or without oxygen and oxygen-containing hydrocarbons (oxygenates). The product gas stream 19a, optionally after precooling in heat exchangers, is cooled in the cooling and condensation unit 20 which may be configured, for example, as a water fluidized bed or as a falling-film condenser, to such an extent that water and high-boiling organic by-products such as high-boiling hydrocarbons and oxygenates condense out and are discharged from the process as stream 21. The uncondensed product gas components are fed to the separating stage 23 as stream 22 in which a removal of low boilers and uncondensable secondary components 24 (when present in product gas stream 19a: hydrogen, carbon oxides, nitrogen, methane, ethane, ethene, propane, propene and oxygen) takes place. The separating stage 23 may be configured as a rectification column or as an absorption/desorption unit. The stream 25 comprising the $C_4$ products of the dehydrogenation, unconverted n-butane and any oxygenates such as furan and maleic anhydride is optionally fed to a further separating stage 26 which may be configured as a rectification column or an absorption/desorption unit. In the separating stage 26, oxygenates and any remaining water traces are removed and discharged from the process as stream 27. The stream 28 composed of butadiene and n-butane which may also comprise small proportions of 1-butene and 2-butene is fed to a further separating stage 29, for example a butadiene scrubbing, and separated there into a stream 31 composed of n-butane and any 1-butene and 2-butene and a stream 30 composed of butadiene. The stream 31 may at least partially be recycled into the non-oxidative catalytic dehydrogenation stage 15.

The invention is illustrated by the examples hereinbelow.

EXAMPLES

Example 1

Preparation of a Dehydrogenation Catalyst Precursor

A solution of 11.993 g of $SnCl_2.2H_2O$ and 7.886 g of $H_2PtCl_6.6H_2O$ in 600 ml of ethanol is poured over 1 000 g of a spalled $ZrO_2/SiO_2$ mixed oxide having a $ZrO_2/SiO_2$ weight ratio of 95:5 from Norton (USA).

The mixed oxide has the following specifications:

Sieve fraction 1.6 to 2 mm; BET surface area: 86 $m^2/g$; pore volume: 0.28 ml/g (from mercury porosimetry measurement).

The supernatant ethanol is taken off on a rotary evaporator using a water jet pump vacuum (20 mbar). Drying is then effected at 100° C. for 15 h followed by calcining at 560° C. for 3 h, each under stationary air. A solution of 7.71 g of $CsNO_3$, 13.559 g of $KNO_3$ and 98.33 g of $La(NO_3)_3.6H_2O$ in 2 500 ml of H2O is then poured over the dry solid. The supernatant water is taken off on a rotary evaporator using a water jet pump vacuum (20 mbar). Drying is then effected at 100° C. for 15 h followed by calcining at 560° C. for 3 h, each under stationary air.

The resulting catalyst precursor has a composition of $Pt_{0.3}Sn_{0.6}Cs_{0.5}K_{0.5}La_{3.0}$ (indices represent weight ratios) on $(ZrO_2)_{95}(SiO_2)_5$ as carrier indices represent weight ratios).

Example 2

Charging of a Dehydrogenation Zone A Reactor and Activation of the Catalyst Precursor 20 ml of the catalyst precursor obtained from example 1 are used to charge a vertical tubular reactor (reactor length: 800 mm; wall thickness: 2 mm; internal diameter: 20 mm; reactor material: internally alonized, i.e. aluminum oxide-coated, steel tube; heating: electrical using an oven from HTM Reetz, LOBA 1100-28-650-2 at a longitudinal midpoint length of 650 mm). The length of the catalyst bed is 75 mm. The catalyst bed is disposed at the longitudinal midpoint of the tubular reactor. The remaining reactor volume above and below is filled with steatite spheres as an inert material (diameter 4–5 mm) which are supported from below on the catalyst base.

The reactor tube is then charged at an external wall temperature along the heating zone of 500° C. with 9.3 l/h (stp) of hydrogen over 30 min. At the same wall temperature, the hydrogen stream is initially replaced over 30 min by a stream of 80% by volume of nitrogen and 20% by volume of air at 23 l/h (STP) and then over 30 min by an identical stream of pure air. While retaining the wall temperature, purging is then effected with an identical stream of $N_2$ over 15 min and finally reduction is once again effected with 9.3 l/h (STP) of hydrogen over 30 min. The activation of the catalyst precursor is then completed.

Example 3

Preparation of an Oxydehydrogenation Catalyst 1750.9 g of aqueous cobalt nitrate solution having a free $HNO_3$ content of 0.2% by weight and a Co content of 12.5% by weight (=3.71 mol of Co) are initially charged in a heatable glass 10 L solid reactor. 626.25 g of solid $Fe(NO_3)_3.9H_2O$ having an Fe content of 14.2% by weight (=1.59 mol of Fe) are dissolved with stirring at room temperature in the initially charged cobalt nitrate solution. 599.5 g of bismuth nitrate solution having a free $HNO_3$ content of 3% by weight and a Bi content of 11.1% by weight (=0.32 mol of Bi) are added to the solution obtained at room temperature. 106.23 g of solid $Cr(NO_3)_3.9H_2O$ (=0.27 mol of Cr) are then added. After heating to 60° C. and further stirring, a red solution (solution A) is obtained.

In a heatable 3 l stirred glas vessel, 2 000 ml of water are initially charged. 2.38 g of KOH (=0.042 mol of K) and 1 124.86 g of $(NH_4)_6Mo_7O_{24}.4H_2O$ (=6.37 mol of Mo) are then added and are dissolved at 60° C. The solution obtained exhibits slight turbidity (solution B).

Solution B is then pumped into solution A while stirring the latter. 102.05 g of $SiO_2$ sol having an $SiO_2$ content of 50% by weight ("Ludox ™" from DuPont =0.85 mol of Si) are added to the dark yellow suspension obtained at 60° C.

The suspension obtained is stirred at 60° C. for 30 minutes and then spray-dried (entrance temperature 370° C., exit temperature 110 to 112° C.). The spray powder obtained is admixed with 4% weight of graphite and then tableted to solid tablets having a diameter of 5 mm and a height of 3 mm. The solid tablets are heat treated at 480° C. for 6 hours in a muffle furnace on a wire sieve (mesh size 3.5 mm) flowed through by air with air flowing through at a rate of 100 l/h. The calcined tablets are comminuted through a wire sieve to give catalyst spall having an average granulate diameter of from 2 to 3 mm.

The oxydehydrogenation catalyst has the nominal composition $Mo_{12}Bi_{0.6}Fe_3Co_7Cr_{0.5}Si_{1.6}K_{0.08}O_x$ (indices represent atomic ratios).

Example 4

Charging of a Dehydrogenation Zone B Reactor 95 ml of catalyst precursor obtained for example 3 are used to charge a vertical tubular reactor (reactor length: 100 cm; wall thickness: 2 mm; internal diameter: 13 mm, reactor material: internally alonized steel tube with a thermowell disposed therein having an external diameter of 2 mm which contains a moveable thermal element; heating: electrical with three different heating zones over the reactor length of 100 cm using heating collars from Winkler, Heidelberg, and a maximum isothermal length of 82 cm is achieved over the middle region of the reactor). The length of the catalyst bed is 82 cm. The catalyst bed is in the isothermal region of the tubular reactor. The remaining reactor volume above and below is charged with steatite spheres as an inert material (diameter 2–3 mm), and the entire reactor tube charge is supported from below on a catalyst base of height 5 cm.

Example 5

Dehydrogenation of n-Butane in the Dehydrogenation Zone A Reactor

The dehydrogenation zone A reactor for example 2 is charged at an external wall temperature along the heating zone of 500° C. with a mixture of 20 l/h (stp) of n-butane, 3.5 l/h (stp) of air, 1.4 l/h (stp) of hydrogen and 10 l/h (stp) of steam as the reaction gas mixture.

The n-butane, air and hydrogen are metered by means of a mass flow regulator from Brooks, while the water is initially metered into an evaporator in liquid form by means of a Kontron HPLC pump 420, evaporated in it and then mixed with the n-butane and the air. The temperature of the charge gas mixture in the charge is 150° C. By means of an REKO pressure regulator at the reactor exit, the exit pressure of the tubular reactor is set to 1.5 bar.

An analytical amount of the product gas mixture A obtained is decompressed to atmospheric pressure and cooled to condense out the steam present. The remaining gas is analyzed by means of GC (HP 6890 with Chem.-Station, detectors: FID; TCD; separating columns: $Al_2O_3$/KCI (Chrompack), Carboxen 1010 (Supelco)). In a corresponding manner, the charging gas mixture is also analyzed.

After an operating time of three days, the analysis results reported in table 1 were obtained:

TABLE 1

|  | Charging gas mixture [% by volume] | Product gas mixture [% by volume] |
|---|---|---|
| Methane |  | 0.07 |
| Ethane |  | 0.05 |
| Ethene |  | <0.01 |
| Propane |  | 0.10 |
| Propene |  | 0.05 |
| $H_2$ | 4.0 | 16.3 |
| $O_2$ | 2.0 | <0.01 |
| $N_2$ | 8.0 | 6.8 |
| CO |  | 0.03 |
| $CO_2$ |  | 0.28 |
| Isobutane |  | 0.11 |
| n-Butane | 57.4 | 33.2 |
| trans-butene |  | 5.7 |
| cis-Butene |  | 4.8 |
| Isobutene |  | 0.08 |
| 1-Butene |  | 4.1 |
| Butadiene |  | 0.52 |
| $H_2O$ | 28.6 | 27.7 |

An n-butane conversion of 32 mol % based on single pass and a selectivity of n-butene formation of 94 mol % corresponds to these values. The selectivity of the butadiene formation corresponds to 3.3%.

Example 6

Dehydrogenation of n-Butane in the Dehydrogenation Zone A Reactor and Subsequent Oxydehydrogenation in the Dehydrogenation Zone B Reactor.

The dehydrogenation zone B reactor from example 4 is heated to a temperature at which the n-butene conversion on single throughput of the reaction gas mixture is >99 mol %, and the internal temperature of the reactor is controlled by means of the thermal elements disposed in the internal thermowell.

The charge consists of a mixture of 150 l/h (stp) of air (=20° C.) and the 34.4 l/h (stp) of product gas mixture A from example 5 (=500° C.). The air is metered in by means of a mass flow regulator from Brooks. The temperature of the charging gas mixture is brought to the reactor external wall temperature. By means of a pressure regulator at the reaction tube exit, the exit pressure of the reactor is set to 1.3 bar.

Downstream of the pressure regulator, the product gas mixture B obtained (temperature =330° C.) is decompressed to atmospheric pressure and analyzed by means of GC (HP 6890 with Chem-Station; detectors: TCD; FID; separating column: Poraplot Q (Chrompack), Carboxen 1010 (Supelco)). The charging gas mixture is analyzed in an identical manner.

After an operating time of 3 days, the results reported in table 2 are obtained.

TABLE 2

|  | Charging gas mixture [% by volume] | Product gas mixture [% by volume] |
|---|---|---|
| Methane | 0.02 | 0.01 |
| Ethane | 0.01 | 0.01 |
| Ethene | <0.01 | <0.01 |
| Propane | 0.02 | 0.02 |
| Propene | 0.01 | <0.01 |
| $H_2$ | 3.5 | 3.5 |
| $O_2$ | 15.7 | 11.1 |
| $N_2$ | 64.3 | 63.5 |
| CO | 0.01 | 1.3 |
| $CO_2$ | 0.06 | 1.3 |
| Isobutane | 0.02 | 0.02 |
| n-Butane | 7.1 | 7.0 |
| trans-Butene | 1.2 | <0.01 |
| cis-Butene | 1.0 | <0.01 |
| Isobutene | 0.02 | <0.01 |
| 1-Butene | 0.9 | <0.01 |
| Butadiene | 0.11 | 2.6 |
| $H_2O$ | 6.0 | 9.6 |

An n-butene conversion of 99 mol % based on single pass and a selectivity of butadiene formation of 80 mol % corresponds to these values.

The overall yield of butadiene over both dehydrogenation zones A and B based on n-butane used is 25%.

Comparative Example

The charging gas mixture described in example 5 is passed directly into the dehydrogenation zone B reactor. Under identical reaction conditions, there is no conversion of the n-butane to butenes or butadiene.

We claim:

1. A process for preparing butadiene from n-butane comprising the steps of
   (A) providing an n-butane-containing feed gas stream,
   (B) feeding the n-butane-containing feed gas stream into a first dehydrogenation zone and nonoxidatively catalytically dehydrogenating n-butane to 1-butene, 2-butene and optionally butadiene to obtain a first product gas steam comprising n-butane, 1-butene and 2-butene, with or without butadiene and secondary components, said nonoxidative catalytic dehydrogenation of n-butane being carried out as an autothermal catalytic dehydrogenation,
   (C) feeding the first product gas stream comprising n-butane, 1-butene and 2-butene, with or without butadiene and secondary components, into a second dehydrogenation zone and oxidatively dehydrogenating 1-butene and 2-butene to butadiene to give a second product gas stream comprising butadiene, n-butane and steam, with or without secondary components,
   (D) recovering butadiene from the second product gas stream.

2. The process as claimed in claim 1, wherein the provision of the n-butane-containing feed gas stream comprises the steps of
  (A1) providing a liquefied petroleum gas (LPG) stream,
  (A2) removing propane and optionally methane, ethane and pentanes from the LPG stream to obtain a butane-containing stream,
  (A3) removing isobutane from the butane-containing stream to obtain the n-butane-containing feed gas stream and optionally isomerizing the removed isobutane to an n-butane/isobutane mixture and recycling the n-butane/isobutane mixture into the isobutane removal.

3. The process as claimed in claim 1, wherein the oxidative dehydrogenation (C) is carried out in more than one state.

4. The process as claimed in claim 1, wherein the recovery (D) of butadiene from the second product gas stream comprises the steps:
  (D1) cooling the product gas stream with water to condense out steam and any high-boiling organic secondary components;
  (D2) removing the low-boiling secondary components contained in the second product gas stream which are selected from the group consisting of hydrogen, carbon monoxide, carbon dioxide, nitrogen, methane, ethane, ethene, propane and propene, to obtain a stream comprising butadiene and n-butane, with or without 1-butene and 2-butene, and with or without oxygenates as further secondary components;
  (D3) optionally removing the oxygenates to obtain a stream comprising butadiene and n-butane, with or without 1-butene and 2-butene;
  (D4) separating the stream comprising butadiene and n-butane, with or without 1-butene and 2-butene, into a stream comprising n-butane, with or without 1-butene and 2-butene, and a stream comprising butadiene;
  (D5) optionally recycling the stream comprising n-butane, with or without 1-butene and 2-butene, into the non-oxidative catalytic dehydrogenation (B).

* * * * *